United States Patent [19]

Hunter

[11] Patent Number: 6,027,954
[45] Date of Patent: Feb. 22, 2000

[54] GAS SENSING DIODE AND METHOD OF MANUFACTURING

[75] Inventor: Gary William Hunter, Avon, Ohio

[73] Assignee: The United States of America as represented by the Administrator of the National Aeronautics and Space Administration, Washington, D.C.

[21] Appl. No.: 09/093,840

[22] Filed: May 29, 1998

[51] Int. Cl.$^7$ ................................................ H01L 21/238
[52] U.S. Cl. ........................... 438/49; 438/92; 438/572
[58] Field of Search .......................... 438/92, 570, 572, 438/573, 575, 580, 582, 48, 49, 93; 257/77, 471, 472, 473

[56] References Cited

U.S. PATENT DOCUMENTS

| | | |
|---|---|---|
| 3,597,270 | 8/1971 | Scott-Monck et al. . |
| 3,645,785 | 2/1972 | Hentzschel . |
| 3,660,154 | 5/1972 | Scott-Monck et al. . |
| 4,622,736 | 11/1986 | Drobny . |
| 5,270,252 | 12/1993 | Papanicolaou . |
| 5,270,554 | 12/1993 | Palmour . |
| 5,296,406 | 3/1994 | Readdie et al. ................... 438/570 |
| 5,362,975 | 11/1994 | von Windheim et al. ............ 257/77 |
| 5,399,988 | 3/1995 | Baliga . |
| 5,442,200 | 8/1995 | Tischler ............................ 257/77 |
| 5,520,753 | 5/1996 | Hunter ............................. 148/430 |
| 5,612,232 | 3/1997 | Thero et al. . |
| 5,635,412 | 6/1997 | Baliga et al. ...................... 438/523 |
| 5,929,523 | 7/1999 | Parsons ............................ 257/750 |

OTHER PUBLICATIONS

Tobias, et al. "Fast Chemical Sensing with Metal Insulator Silicon Carbide Structures" IEE Elector Device Letters, vol. 18; pp.287–289 (Jun. 6, 1997).

Karlstein, et al. "Electrical Properties of MIS Structures on 6N–Sic". Linkoping University, Conference pp. X–17 to X–22. (Jun. 5–10, 1994).

Primary Examiner—Savitri Mulpuri
Attorney, Agent, or Firm—Kent N. Stone

[57] ABSTRACT

A diode for sensing hydrogen and hydrocarbons and the process for manufacturing the diode are disclosed. The diode is a Schottky diode which has a palladium chrome contact on the C-face of an n-type 6H Silicon carbide epilayer. The epilayer is grown on the C-face of a 6H silicon carbide substrate. The diode is capable of measuring low concentrations of hydrogen and hydrocarbons at high temperatures, for example, 800° C. The diode is both sensitive and stable at elevated temperatures.

5 Claims, 2 Drawing Sheets

```
┌─────────────────────────────────────┐
│  DEPOSITING AN n-TYPE 6H SiC EPILAYER │
│  ON A C-FACED 6H SiC SUBSTRATE       │
└─────────────────────────────────────┘
                 │
┌─────────────────────────────────────┐
│       ETCHING THE EPILAYER           │
└─────────────────────────────────────┘
                 │
┌─────────────────────────────────────┐
│   RINSING THE EPILAYER WITH          │
│   DEIONIZED WATER                    │
└─────────────────────────────────────┘
                 │
┌─────────────────────────────────────┐
│  BLOW DRYING THE EPILAYER WITH N2 GAS│
└─────────────────────────────────────┘
                 │
┌─────────────────────────────────────┐
│   DEPOSITING A $Pd_{.9}Cr_{.1}$ CONTACT│
│   ON THE EPILAYER                    │
└─────────────────────────────────────┘
                 │
┌─────────────────────────────────────┐
│  DEPOSITING AN ALUMINUM BACKSIDE     │
│  CONTACT ON THE 6H SiC SUBSTRATE     │
└─────────────────────────────────────┘
```

FIG. 2

GAS SENSING DIODE AND METHOD OF MANUFACTURING

ORIGIN OF THE INVENTION

The invention described herein was made by an employee of the United States Government and may be manufactured and used by or for the Government for Government purposes without the payment of any royalties thereon or therefor.

FIELD OF THE INVENTION

The instant invention is a Schottky diode. Its principal use is the measurement of hydrogen and hydrocarbons occurring at low concentrations and high temperatures.

BACKGROUND OF THE INVENTION

U.S. Pat. No. 5,270,252 to Papanicolaou is a Schottky diode on beta silicone carbide. The metals taught in the Papanicolaou disclosure are platinum, tungsten, titanium tungsten, gold and aluminum. The Schottky diode of the Papanicolaou disclosure is used for high temperature semiconductor applications and, in particular, it is used as a rectifying diode.

U.S. Pat. No. 5,612,232 to Thero, et al. is a Schottky diode for use in high temperature applications but it cannot be used as a gas sensor. Thero, et al. teaches the use of a silicon carbide semiconductor with nickel and tungsten as metals.

U.S. Pat. No. 4,622,736 to Drobny discloses Schottky diodes for use in connection with a silicon semiconductor. Tungsten, titanium-tungsten, and vanadium are the metals used in the invention. The Drobny Schottky diode is not a gas sensor.

The development of a Schottky diode structure has been reported by the researchers at Linkoping University. The structure of the Linkoping sensor is Pt on TaSix on SiO2 on SiC. The Pt/TaSix/SiO2 thicknesses are 100 nm/10 nm/5 nm respectively. The sensor responses are stable and fast but they are not highly sensitive.

SUMMARY OF THE INVENTION

The instant invention discloses a Schottky diode which includes an alpha silicon carbide substrate, an alpha silicon carbide epilayer, a backside contact, and a palladium chrome contact. The silicon carbide epilayer is an n-type carrier as is the silicon carbide substrate. The epilayer is grown on a commercially available n-type 3.5° off-axis polished c-FACE 6H—Sic substrate. The epilayer surface was etched by a dilute hydrofloric solution, rinsed with deionized water and blown dry with nitrogen prior to the deposition of the palladium chrome film thereon. Approximately 400 Angstroms of the palladium chrome alloy are magnetron-sputter deposited onto the C-face of the epilayer to form a palladium chrome/silicon carbide diode. The ratio of the palladium to chrome is controlled during the deposition thereof.

In the preferred embodiment the palladium chrome deposition is 90 atomic percent palladium and 10 atomic percent chrome. A backside substrate contact is formed by sputtering aluminum thereon.

The palladium chrome contact surface is a catalytic material in the presence of hydrogen. The presence of hydrogen results in an increased current flow through the diode with a given bias voltage applied to the diode. Hydrogen dissociates when it reacts with the palladium chrome.

It is an object of the invention to provide a sensor which is stable and sensitive at high temperatures of 425° C. and above.

It is a further object of the present invention to provide a palladium chrome contact on an alpha 6H silicon carbide substrate with a metal backside contact.

It is an object of the present invention to provide a gas sensor using an alloy on the C-face of a silicon carbide epilayer on a silicon carbide substrate.

It is an object of the present invention to provide a sensor which is stable and sensitive following exposure to high temperatures for long periods of time.

It is an object to provide a Schottky diode employing silicon carbide as the semiconductor to detect hydrogen and hydrocarbons at low concentrations.

It is an object to provide a hydrogen and/or hydrocarbon sensor which can be used at elevated temperatures for prolonged periods of time for use in catalytic combustion control systems or other applications which depend on the presence of hydrogen or hydrocarbons.

BRIEF DESCRIPTION OF THE DRAWINGS

Drawing

Figure 1:
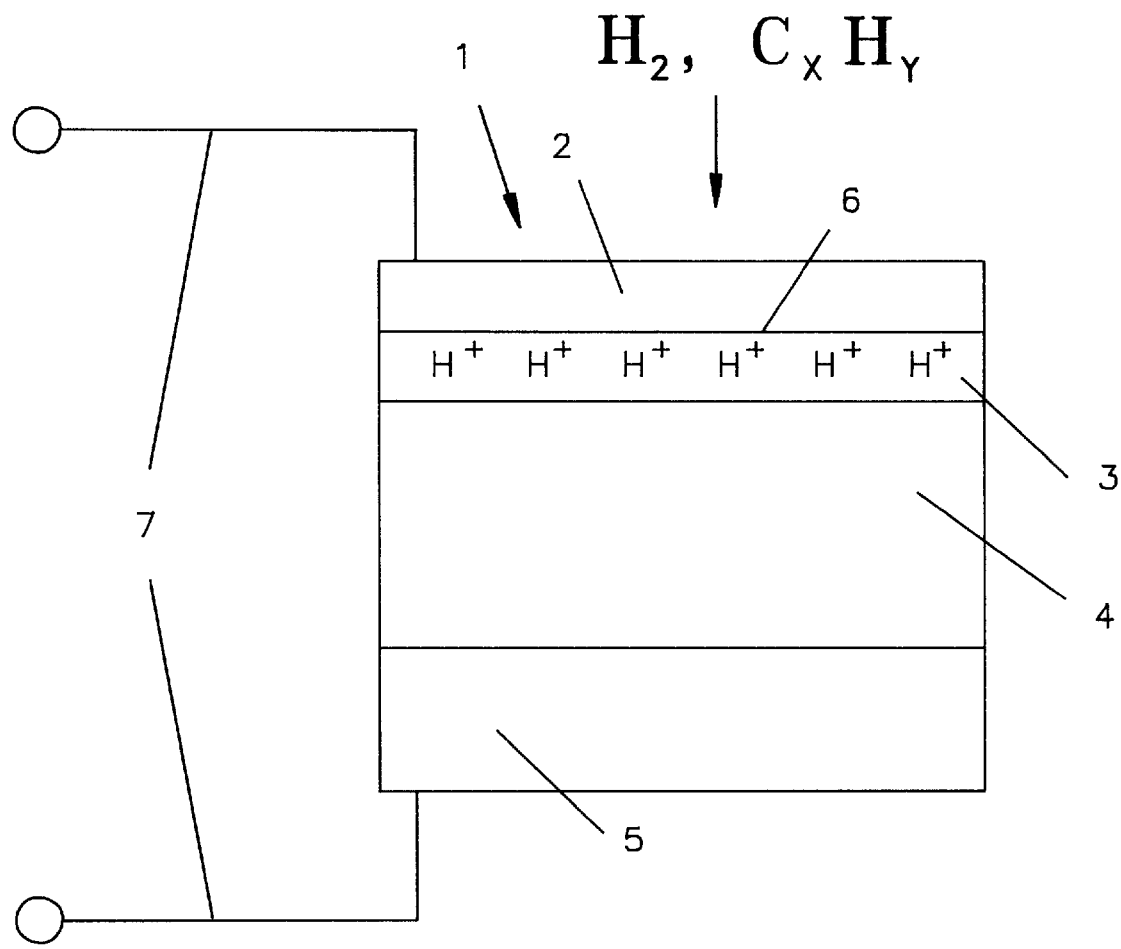
FIG. 1 illustrates the $Pd_{0.9}Cr_{0.1}$ contact on the C-face of an α Silicon Carbide epilayer on the C-face of the α Silicon Carbide substrate. A backside metal contact is also shown.

Drawing FIG. 2 schematically illustrates the process for manufacturing the Schottky diode.

DETAILED DESCRIPTION OF THE INVENTION

A Schottky diode is formed by the junction of a metal and a semiconductor. Other diodes are formed by the junction of a p-type and an n-type semiconductor.

FIG. 1 is a schematic representation of the structure of the invention. FIG. 2 is a schematic of the process used (described above) to manufacture the instant invention. The advantage of the Schottky diode 1 of the present invention is that a large signal difference is obtained in response to a corresponding small concentration of hydrogen or hydrocarbons in high temperature applications. The Schottky diode of the present invention has a high gain. In other words, the Schottky diode 1 used as a high temperature sensor of hydrogen and hydrocarbons is sensitive and stable. Referring to FIG. 1, the Schottky diode of the present invention uses an α silicon carbide (SiC) substrate 4 and an α silicon carbide (SiC) epilayer 3.

Epilayer 3 is 4–5 $\mu$m thick and is grown or deposited on the silicon carbide (SiC) substrate 4 by chemical vapor deposition. Silicon carbide is used because it has superior thermal properties and does not degrade at temperatures as high as 800° C. Epilayer 3 and substrate 4 are both n-type SiC. Substrate 4 is commercially available 3.5° off-axis polished C-face 6H—Sic.

The epilayer 3 is a n-type C-faced 6H—Sic. Reference numeral 6 indicates the C-face of the epilayer 3. Once deposited on the substrate, the epilayer 3 is etched with hydrofloric acid and is then rinsed with deionized water. These procedures are to chemically clean the SiC surface. Next, the epilayer is blown dry with gaseous nitrogen ($N_2$). Some slight oxidation of the surface of the epilayer may occur in this process without any degradation of the Schottky diode for use as a sensor of hydrogen and hydrocarbons.

When dried, the C-face of the epilayer has an alloy 2 deposited thereon. In the preferred embodiment the alloy 2 is palladium chrome (PdCr). The palladium chrome alloy is deposited onto the C-face of the epilayer using magnetron sputtering. Approximately 400 Angstrums of palladium chrome are used in the preferred embodiment. However, 300–1000 Angstroms of an alloy such as palladium chrome may be used. Other forms of physical deposition can be used as well such as evaporation. Chemical vapor deposition may also be used. The ratio of palladium is 90 atomic percent to 10 atomic percent chrome. This ratio may vary from about 70 to 95 atomic percent palladium to 5 to 30 atomic percent chrome. Palladium dissociates hydrogen. A backside metallic contact 5 is affixed to the SiC substrate 4 by magnetron sputtering. In the preferred embodiment the contact 5 is aluminum.

The thermal stability of the Schottky diode of the preferred embodiment, to wit, $Pd_{0.9}Cr_{0.1}$/6H—Sic, is improved compared to a Pd/SiC diode. Further, the response of a $Pd_{0.9}Cr_{0.1}$/6H—Sic diode to hydrogen is stable after long heating periods.

Reference numeral 7 indicates the sensor electrical connections. A bias voltage is applied to the Schottky diode 1 (i.e., the sensor) in operation and the presence of hydrogen or hydrocarbons causes a change in the current measured in the circuit.

The foregoing description of the invention has been set forth by way of example only and in no way limits the scope of the invention. The scope of the invention is set forth in the attached claims.

What is claimed is:

1. A process for manufacturing a Schottky diode having an n-type polished 6H silicon carbide substrate, an n-type 6H silicon carbide epilayer, a 400 Angstrom thick palladium chrome contact and a backside contact, comprising the steps of:

depositing an n-type C-faced 6H silicon carbide epilayer on a polished C-face of a 6H silicon carbide substrate;

etching said epilayer with an acid solution;

rinsing said epilayer;

drying said epilayer;

depositing palladium and chrome on said epilayer; and, depositing a metallic backside contact on said 6H silicon carbide substrate.

2. A process as claimed in claim 1 wherein said step of depositing palladium and chrome comprises depositing 90 atomic percent palladium and 10 atomic percent chrome.

3. A process as claimed in claim 2 wherein said step of depositing a metallic backside contact comprises depositing an aluminum backside contact.

4. A process as claimed in claim 3 wherein said step of depositing palladium and chrome comprises magnetron sputtering said palladium and chrome.

5. A process as claimed in claim 4 wherein said step of depositing an aluminum backside contact comprises magnetron sputtering said aluminum backside contact.

* * * * *